(12) United States Patent
Kritzler

(10) Patent No.: US 8,196,248 B2
(45) Date of Patent: Jun. 12, 2012

(54) ENDOSCOPE CLEANING PAD

(75) Inventor: Steven Kritzler, Cronulla (AU)

(73) Assignee: Novapharm Research (Australia) Pty Ltd, New South Wales (AU)

( * ) Notice: Subject to any disclaimer, the term of this patent is extended or adjusted under 35 U.S.C. 154(b) by 1748 days.

(21) Appl. No.: 10/553,852

(22) PCT Filed: Mar. 30, 2004

(86) PCT No.: PCT/AU2004/000404
§ 371 (c)(1),
(2), (4) Date: Oct. 19, 2005

(87) PCT Pub. No.: WO2004/094080
PCT Pub. Date: Nov. 4, 2004

(65) Prior Publication Data
US 2007/0033753 A1    Feb. 15, 2007

(30) Foreign Application Priority Data
Apr. 22, 2003    (AU) .............................. 2003901917

(51) Int. Cl.
*B08B 1/00* (2006.01)
(52) U.S. Cl. .................... 15/104.93; 15/115; 15/104.94
(58) Field of Classification Search ............... 15/104.93, 15/104.94, 115, 118, 228, 229.4, 229.5, 244.4, 15/244.3, 224.1
See application file for complete search history.

(56) References Cited

U.S. PATENT DOCUMENTS

| | | | |
|---|---|---|---|
| 4,098,728 A | 7/1978 | Rosenblatt | |
| 4,517,702 A | 5/1985 | Jackson | |
| 5,223,166 A | 6/1993 | Disch et al. | |
| 5,382,297 A | 1/1995 | Valentine et al. | |
| 5,489,531 A | 2/1996 | Benson | |
| 6,235,692 B1 | 5/2001 | Scoville | |
| 7,235,250 B2 * | 6/2007 | Padlo et al. ................ | 424/401 |
| 2002/0120242 A1 * | 8/2002 | Tyrrell et al. ............... | 604/364 |
| 2003/0077307 A1 * | 4/2003 | Klofta et al. ................ | 424/401 |
| 2004/0076660 A1 * | 4/2004 | Padlo et al. ................ | 424/443 |
| 2004/0266643 A1 * | 12/2004 | Gardner et al. ............. | 510/337 |
| 2007/0033753 A1 * | 2/2007 | Kritzler ..................... | 15/104.93 |

FOREIGN PATENT DOCUMENTS

| | | |
|---|---|---|
| GB | 2 360 041 A | 9/2001 |
| JP | 08 256978 | 10/2008 |
| WO | WO-01/76366 | 10/2001 |
| WO | WO 01/76647 A1 | 10/2001 |
| WO | WO 02/07789 A1 | 1/2002 |
| WO | WO 02/18530 A1 | 3/2002 |
| WO | WO 2004094080 A1 * | 11/2004 |

\* cited by examiner

*Primary Examiner* — Lee D Wilson
(74) *Attorney, Agent, or Firm* — Jeffrey D. Hsi; Dwight D. Kim; Edwards Wildman Palmer LLP

(57) ABSTRACT

A cleaning device for cleaning a medical instrument such as an endoscope, which includes a fabric, wipe, or sponge impregnated with a composition which comprises: an enzyme such as a protease, alcalase, cellulase, lipolase: a surfactant and a humectant present in an amount to ensure that sufficient water is absorbed to reduce any hazard which would arise from use of the enzyme in dry form while maintain activity of the enzyme during storage. The cleaning device is adapted to remove at least a portion of externally adherent soiling on a surgical instrument by mechanical wiping; and to redistribute any remaining external soiling such that it is distributed as a film of thinner and more uniform thickness than on the unwiped instrument. The invention also relates to packaging of the cleaning device, and methods of use thereof.

40 Claims, 1 Drawing Sheet

ENDOSCOPE CLEANING PAD

TECHNICAL FIELD

This invention relates to cleaning devices and methods, and more particularly to a method and apparatus for cleaning the exterior of contaminated surgical instruments. The device has been developed for use in cleaning the exterior of rigid or flexible endoscopes and will be described primarily with reference to that use.

BACKGROUND ART

An endoscope is an elongate tubular instrument that may be rigid or flexible and which incorporates an optical or video system and light source. Typically, the endoscope is configured so that one end can be inserted to some depth into a surgical incision or body cavity via an incision or orifice whereby surfaces on or near the internally inserted end of the endoscope may be viewed by an external observer. A commonly used endoscope is a flexible endoscope called a colonoscope and is used for diagnostic procedures of the human colon. The colon insertion portion of the instrument is approximately two meters long and has one or more hollow channels, or lumens.

Because of the high cost of endoscopes and the need to avoid cross infection from one patient to the next, each endoscope must be thoroughly cleaned and disinfected or sterilised after each use. This procedure is time consuming and presents major difficulties because the endoscope becomes significantly contaminated with biological material from the patient for example mucus, faeces, blood, pieces of tissue and the like.

A typical cleaning procedure involves rinsing and scrubbing the endoscope exterior under running water for some time to remove gross contaminants, subsequently soaking the endoscope in a suitable cleaning bath for 2 to 10 minutes, rinsing the instrument, drying the instrument and then disinfecting it. On some occasions the gross contaminants on the outside of the instrument are inadequately removed by rinsing and the subsequent cleaning bath prior to disinfection. This inadequate external cleaning then compromises the disinfection or sterilisation step since it is impossible to reproducibly disinfect or clean a dirty instrument.

Because the time required for cleaning and disinfection or sterilisation is often longer than the duration of the procedure in which the endoscope is used, capital must be expended on a plurality of instruments or else cleaning becomes the determining factor as to the rate at which procedures can be performed. Moreover a considerable amount of time and materials are consumed in cleaning the brushes and other apparatus used to clean the endoscope including the lumens. Recently attention has been paid to improved methods of cleaning the interior of the lumen (see eg our co-pending application PCT/AU99/00669), however that method is not applicable to the exterior surface. Cleaning the exterior remains a critical, difficult and labour intensive task. Various sophisticated chemical and biochemical products, for example enzyme/detergent compositions, have been developed for use as pre-soaks to loosen contaminants from the exterior surface and to facilitate their subsequent removal by scrubbing. The ultimate efficacy of such treatments is heavily dependant on (a) how diligently rinsing and scrubbing is performed; (b) how much debris is on the surface after the examination and the nature of such debris; and (c) whether the soiled instrument has been allowed to dry prior to cleaning and, if so, the temperature at which this drying took place.

Moreover, the present Applicant has found that rinsing and scrubbing with brushes often serves merely to rearrange deposits on the surface of the instrument rather than to remove them. Furthermore, the use of brushes may create a contaminated aerosol which can endanger health-care workers in the vicinity.

Any discussion of the prior art throughout the specification should in no way be considered as an admission that such prior art is widely known or forms part of common general knowledge in the field.

It is an object of the present invention to overcome or ameliorate at least one of the deficiencies of the prior art, or to provide a useful or more convenient alternative. It is an object of certain preferred embodiments of the invention to provide a device and methods to improve the speed and/or efficiency of cleaning endoscopes and the like. It is an object of certain highly preferred embodiments of the invention to provide an inexpensive effective device which can be manufactured inexpensively and which can be disposable after a single use.

DESCRIPTION OF THE INVENTION

According to a first aspect the invention provides a cleaning device for surgical instruments including a fabric, wipe, or sponge impregnated with a composition comprising an enzyme, a surfactant, and a humectant. As herein used the term "sponge" includes polymeric open and closed cell foam materials as well as natural sponge.

Preferred embodiments of the invention are adapted for use in cleaning the exterior tubular surface of an endoscope or external surface of another surgical instrument.

Preferably the device is impregnated with a composition comprising a combination of enzymes selected from proteases, alcalases, cellulases lipolases and mixtures thereof.

The enzymes used in examples and formulations hereafter are commercially available aqueous enzyme solutions or suspensions and not pure enzymatic protein.

Preferably, the total quantity of enzyme solution or suspension is present in an amount of 5 to 25% w/w of the composition, and more preferably in an amount of 10 to 20% w/w of the composition.

Preferably, the humectant is present in the composition in an amount of 1 to 10% w/w of the composition and more preferably in an amount of 4 to 7% w/w of the composition.

Desirably, the surfactant includes at least one non-ionic surfactant.

Preferably, the non-ionic surfactant is present in the composition in an amount of 5 to 45% w/w. It is also preferred that if an anionic surfactant is present in the composition it will be in an amount of 5 to 15% w/w. Preferably, the total surfactant in thae composition is in an amount of 15 to 45% w/w.

Desirably, the device is adapted to contact a substantial arc of the circumference of a tubular portion of the instrument, and is adapted to slide axially along the length of the tubular portion so as to wipe the surface. Preferably the device engages an arc of up to 360 degrees of the external circumference of a tubular portion of the instrument and is resiliently deformable in the radial direction. More preferably, the device is fabricated from hydrophilic fibres.

Preferred embodiments of devices according to the invention remove most of the externally adherent soiling by a mechanical wiping action, but more importantly the device serves to redistribute any remaining external soiling so that the contamination which is not removed is distributed as a film of thin and uniform thickness. That film is thereby adapted to achieve more efficient and speedy soil removal by enzyme digestion.

According to a second aspect the invention provides a device for use in cleaning the exterior surface of a tubular endoscope requiring cleaning, said device including a pad of hydrophilic fibres having a groove extending from one end of the pad to an opposite end and adapted resiliently to engage a portion of the endoscope exterior surface, the pad being adapted alone or with a complementary pad to substantially encircle said portion and being resiliently deformable so as to engage the surface of the encircled portion, whereby to uniformly wipe said exterior surface as the device is slid longitudinally along the endoscope tube.

Preferably the pad is formed of a needle felt and has two spaced apart parallel grooves each of arcuate cross-section which may be folded into alignment on opposite sides of a tubular axis to form a tubular tunnel resiliently engaging the endoscope exterior about its circumference.

In preferred embodiments a cleaning device according to the second aspect is fabricated from a non woven fabric and is impregnated with a plurality of enzymes, a plurality of surfactants and at least one humectant. In a highly preferred form of this embodiment the non woven fabric is packed as a roll, or perforated roll, of "wipes" in a dispensing canister permitting one or more wipes to be drawn from the dispenser and tom off for use and then disposal.

According to a third aspect the invention provides a package containing a cleaning device for surgical instruments, said cleaning device including a single use fabric or sponge impregnated with an enzyme, a surfactant, and a humectant.

In preferred embodiments according to the third aspect, the package is moisture permeable.

The present applicant has found that a non woven fabric impregnated with an enzyme composition provides an efficient means for wiping clean the outside of an endoscope. In initial experiments, the non woven was impregnated with a known enzyme/detergent composition. Packing the impregnated product dry maintained the activity of the enzymes during storage and transport of the product but carried an unacceptable risk of releasing dry proteases into the atmosphere, an inhalation safety hazard, when the package was opened. Accordingly, it was thought necessary to moisten the impregnating enzyme/detergent composition. This in turn required that each moist impregnated fabric be packaged within a water impermeable barrier to prevent the device from drying put. However that added significantly to the cost. The inventor then discovered that if the device was impregnated with a humectant, a moisture permeable package could be employed and the humectant ensured that sufficient water was absorbed in the composition to prevent dry proteases from becoming a hazard when the package was opened or the product used. Surprisingly, the activity of the enzymes was maintained during storage. The product can then be simply removed from its package, wet under a tap, and then wrapped around the end of an endoscope. The device is then slid along the length of the endoscope to remove soiling. The product can be manufactured and packaged at sufficiently low cost to be considered disposable after a single use.

A further advantage of devices according to the invention is that enzymatic action commences during the scrub phase, that is to say at an earlier stage in the cleaning process than has been practiced in the past, and thereby prolonging the overall enzyme treatment time and in turn increasing cleaning efficacy.

According to a fourth aspect the invention provides a method of cleaning the exterior surface of a surgical instrument in need thereof, said method including the steps of:

(i) wiping the exterior surface, wherein a resilient pad or a wipe is pressed against an exterior surface of the surgical instrument and slid longitudinally to mechanically remove gross soiling and at the same time redistribute any residue remaining to a substantially uniform thickness, while at the same time;

(ii) subjecting the surface to treatment with an enzyme and a surfactant.

BEST MODES FOR CARRYING OUT THE INVENTION

Figure 1:
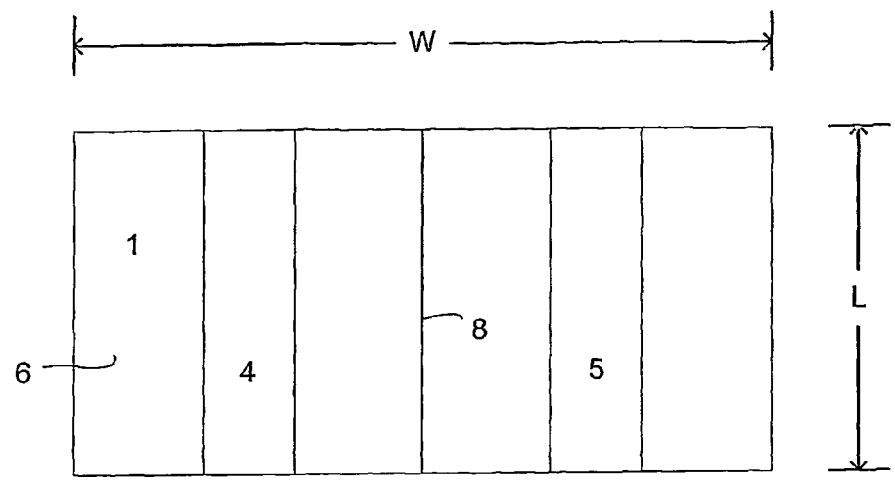
FIG. 1 is a schematic diagram showing a first embodiment of a device according to the invention in plan view.
Figure 2:
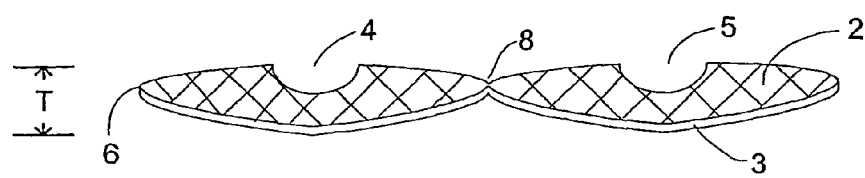
FIG. 2 is a schematic diagram showing the embodiment of FIG. 1 in cross sectional elevation.

A preferred embodiment will now be described by way of example only with reference to the drawings. The embodiment exemplified in FIGS. 1 and 2 provides a cleaning device in the form of a pad 1 made from a non woven needle felted polyester or viscose fabric 2 bonded to a woven backing which can be made of polyester or polypropylene fibres 3 on one surface. Pad 1 is of substantially rectangular shape having a width dimension "w" of approximately 133 mm and a length dimension "l" of approximately 9 cm, and is approximately 15 mm thick at its thickest dimension "t". The pad is heat sealed around its perimeter and has two arcuate grooves 4, 5 of approximately semicircular cross-section formed by heat moulding and extending in the length direction centred at intervals of approximately one quarter "w" and three quarters "w" from one edge 6. The grooves each have a radius of approx. 7 mm. In addition there is a fold groove 8 extending in the length direction on the midline, i.e. at a distance of half "w" from side edge 6.

Figure 3:
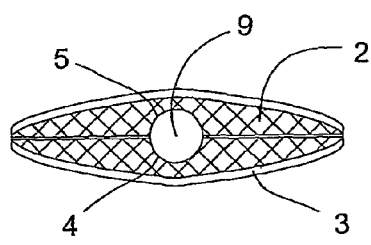
FIG. 3 is a schematic diagram showing the device of FIGS. 1, 2 in cross-sectional elevation wrapped circumferentially around an endoscope tube.

In use, an endoscope tube is pressed into groove 4 bringing the pad into contact with a semicircle of the endoscope cross-ssection. The pad is then folded over, as shown schematically in FIG. 3, so that groove 5 contacts the remainder of the cross-section. FIG. 3 shows the pad of FIGS. 1, 2 folded along groove 8 so that grooves 4, 5 are brought into registration forming a cylindrical tunnel about an endoscope tube 9 which in the present example has an outside diameter of approx. 14 mm. The polyester or viscose needle felt structure has a degree of resilience, and the pad may be held around the endoscope tube in a manner which compresses the pad exerting a resilient force acting radially towards the tubular axis of the endoscope. The pad is thus pressed against the exterior endoscope surface while the device is slid longitudinally to mechanically remove gross soiling and at the same time the pad redistributes any residue evenly on the surface, that is to say distributes it substantially uniformly in thickness about the circumference and along the length. It will be understood that the dimensions of the pad and grooves may be altered to suit different endoscopes, but an advantage of the design is that the resilience of the pad accommodates a range of endoscope diameters.

An example of a suitable pad is composed of two different fibres, the first of which is polyester or viscose of 3 denier and a fibre length of 51 mm and the second of which is polypropylene of 2 denier and a fibre length of 51 mm. The ratio of the two fibres is 70% polyester or viscose and 30% polypropylene. These two fibres are mixed till homogeneous and then tangled by the needling technique until a low density web with substantially no free fly away fibres has been formed.

The thickness of the web is controlled by the amount of fibre and the needling equipment employed, however a web of between 5 nm and 15 mm has proved to be ideal for the application. The dry web is impregnated with a hygroscopic enzyme cleaning formulation containing one or more enzymes, one or more surfactants, an enze stabilising system and can contain a disinfectant compatible with the enzymes employed.

In a second embodiment not illustrated the pad is provided with a slit through which an endoscope tube may be threaded and held in a clamped manner to similar effect. Although it is preferred to provide a pad with two grooves and to fold the pad, two separate pads each with a groove could be similarly employed.

Devices may be manufactured with grooves of different dimensions to accommodate instruments of differing diameter, although the resilience of the pad permits the device to be used satisfactorily with instruments over a range of diameters.

In highly preferred embodiments, the pad is impregnated with a composition such as that set out in example 1.

Example 1

|  | % w/w |
| --- | --- |
| Non-ionic surfactant (e.g. nonyl phenol ethoxylate) | 10.0 |
| Anionic surfactant (e.g. linear alcohol sulphonate) | 10.0 |
| Preservative (e.g. magnesium thionate) | 0.15 |
| Humectant (e.g. Calcium chloride hexahydrate) | 4.5 |
| Protease | 10.0 |
| Alcalase | 3.5 |
| Cellulase | 1.0 |
| Lipolase | 0.7 |
| Propylene Glycol | 12.0 |
| Tap water to 100 | |

The activity units for the enzymes used in Example 1 are:

| Protease | 16 KNPU/gm or 5 AU/gm |
| --- | --- |
| Amylase | 300 KNU/gm |
| Cellulase | 1000 ECU/gm |
| Lipase | 100 KLU/gm |

Those skilled in the art will appreciate that enzymes are supplied on the basis of activity units rather than protein concentration, and that the units used to define activity differ depending upon the specific chemistry of the enzyme involved. However, those skilled in the art will be familiar with reformulating enzymes of different activity and will be readily able to adapt the formulations of the present invention according to the specific circumstances.

Example 2

Example 2 is identical to example 1 except that 4.5% w/w glycerine is substituted for Calcium chloride hexahydrate.

The surfactants, preservatives and enzymes can be varied in composition and quantity in accordance with formulation and compatibility requirements. Importantly, the composition contains a humectant. Suitable humectants may for example be calcium chloride, sodium chloride, glycerine, borax, ethylene glycol or such like. The humectant may also be a surfactant.

One or more of the pads is packed together in a package which may be water permeable This together with the presence of the humectant serves to keep the composition sufficiently moist to avoid dry particles of enzyme from being released into the air when the package is opened. Optionally, the formulation may contain a disinfectant compatible with the enzymes, for example a quaternary ammonium compound.

The loading of composition on the fabric, wipe or sponge can be varied as desired. The composition can be applied in any ratio, from a small amount, 1 to 5% of the weight of the fabric, wipe or sponge right up to an amount which fully saturates the pad or wipe.

In use, a device according to the invention is removed from its package and may be further dampened with water, wrapped circumferentially around an end of the endoscope and wiped along the endoscope length to remove soiling. The pad is then disposed of in a suitable manner. The enzymes commence digestive action immediately. The endoscope, now free of most of the adherent soiling, is further cleaned in a suitable cleaning solution and then disinfected or sterilized. Because any residue is now distributed as a thin film of uniform thickness, subsequent treatment in a bath is effective in a shorter time than would be the case if the exterior were merely scrubbed with a brush.

Although the above discussed embodiment employs a viscose fibre pad, it is envisaged that the pad could be made from a polymeric foam or suitable textile paper or hybrid structure. However it is desirable that the device be not too absorbent since it is desirable that the instrument remain moist.

A very highly preferred embodiment uses a roll of non-woven fabric "wipes". The roll is, for example, 8 meters long, and 10 cm wide and is perforated at 10 cm intervals, so that up to 80 wipes of 10 cm x 10 cm can be torn from a free end of the roll. Alternatively, the product may be supplied in a canister containing 200 wipes in an 8 meter roll. The non woven fabric used in the wipes is a made from a cellulosic fibre (for example viscose) web. This web is then treated with an aqueous dispersion of a flexible cross-linking acrylic latex. The aqueous dispersion is such as to incorporate up to 15% by weight and preferably about 8% by weight of dry acrylic polymer. Upon the addition of a suitable proportion of a cross-linking catalyst the non-woven structure is saturated with the latex/catalyst dispersion and excess dispersion drained from the structure by gravity, or else squeezed out with the assistance of compression rollers whereupon the structure is then dried at a temperature appropriate to induce cross-linking. Upon cooling a bonded, non-woven, open structured web has been achieved, and has the following specification:

Basic mass (g./sq.m): about 42.5
Dry strength: (g/25 mm): 225
Thickness (um/4 ply): 1270
Absorbency (g/5 g): 420

The roll of wipes is contained in a dispensing canister which is preferably moulded from plastic, has a diameter only slightly larger than the roll diameter and has a replaceable closure which seals with the container. Under the replaceable closure is a canister lid or wall provided with one or more slits disposed about the roll axis through which an end of the roll can be dispensed. A formulation such as shown in example 1 or example 2, and containing an enzyme and a humectant, is added to the container in sufficient quantity to impregnate the non woven fabric. Thereafter, wipes may be pulled from the canister and torn off the roll end as needed. In use, an impregnated wipe is held in the gloved hand, moistened under a tap, and then used to wipe the exterior surface of an instrument to be cleaned. By virtue of the slits the container is moisture permeable. An additional outer removable closure may be provided to exclude particles and to inhibit moisture loss. However the slits ensure that the moisture can permeate the package.

As will be apparent to those skilled in the art from the teaching hereof use of a device or wipe according to the invention provide a major advance in convenience and efficacy over existing methods for cleaning endoscopes. The device or wipe may be used for cleaning other medical and non medical instruments, surfaces, and the like. The device or wipe may be embodied in other forms or be manufactured from other materials without departing from the inventive concept herein disclosed and the formulation may be varied without departing from the invention.

The invention claimed is:

1. A cleaning device for cleaning a medical instrument including: a fabric, wipe, or sponge impregnated with a composition comprising at least one enzyme, wherein the enzyme is present as a solution or a suspension in an amount of 5 to 25% w/w of the composition, a surfactant and a humectant, wherein contaminants on said instrument are removed or distributed by said cleaning device so as to enhance the speed and efficiency of enzyme digestion.

2. A cleaning device according to claim 1 further including a disinfectant compatible with said at least one enzyme.

3. A cleaning device according to claim 1 wherein the at least one enzyme is selected from protease, alcalase, cellulase, lipolase, and combinations thereof.

4. A cleaning device according to claim 3 wherein the enzyme is present as a solution or a suspension in an amount of 10 to 20% w/w of the composition.

5. A cleaning device according to claim 1 wherein the humectant is selected from calcium chloride, sodium chloride, glycerine, borax, ethylene glycol, propylene glycol and combinations thereof.

6. A cleaning device according to claim 5 comprising glycerine as a humectant.

7. A cleaning device according to claim 1 wherein the humectant is present in an amount to ensure that sufficient water is absorbed to reduce any hazard which would arise from use of the enzyme in dry form.

8. A cleaning device according to claim 1 wherein the humectant is present in an amount to maintain activity of the enzyme during storage.

9. A cleaning device according to claim 8 wherein the humectant is present in the composition in an amount of 1 to 10% w/w of the composition.

10. A cleaning device according to claim 9 wherein the humectant is present in the composition in an amount of 4 to 7% w/w of the composition.

11. A cleaning device according to claim 1 wherein the surfactant includes at least one non-ionic surfactant.

12. A cleaning device according to claim 11 wherein the non-ionic surfactant is present in the composition in an amount of 5 to 45% w/w.

13. A cleaning device according claim 1 wherein the surfactant is a synthetic or natural alcohol ethoxylate.

14. A cleaning device according to claim 1 wherein the surfactant includes at least one anionic surfactant.

15. A cleaning device according to claim 14 wherein the anionic surfactant is present in the composition in an amount of 5 to 15% w/w.

16. A cleaning device according to claim 14 wherein the anionic surfactant is a hydrocarbon sulphonate or sulphate.

17. A cleaning device according to claim 1 wherein the total surfactant in the composition is in an amount of 15 to 45% w/w.

18. A cleaning device according to claim 1 further including a preservative.

19. A cleaning device according to claim 1 adapted to
i) remove at least a portion of externally adherent soiling on a surgical instrument by mechanical wiping; and
ii) to redistribute any remaining external soiling such that it is distributed as a film of thinner and more uniform thickness than on the unwiped instrument.

20. A cleaning device according to claim 1 adapted for use in cleaning an exterior tubular surface of a surgical instrument.

21. A cleaning device according to claim 1 adapted for use in cleaning an exterior tubular surface of an endoscope.

22. A cleaning device according to claim 1 adapted to contact a substantial arc of an external circumference of a tubular portion of the instrument.

23. A cleaning device according to claim 22 adapted to engage an arc of about 360 degrees of an external circumference of a tubular portion of the instrument and which is resiliently deformable in a radial direction.

24. A cleaning device according to claim 1 adapted to slide axially along the length of a tubular portion of the instrument so as to wipe the surface thereof.

25. A cleaning device according to claim 1 fabricated from hydrophilic fibres.

26. A cleaning device according to claim 1 fabricated from polymeric material.

27. A cleaning device according to claim 1 composed of viscose fibres and polypropylene fibres.

28. A cleaning device according to claim 27 wherein the viscose fibres and polypropylene fibres form a homogeneous mixture tangled by a needling technique to form a low density web with substantially no free fly away fibres.

29. A cleaning device according to claim 1 in the form of a wipe, or roll of wipes, fabricated from a polymeric foam, textile, paper or hybrid material.

30. A cleaning device for cleaning a medical instrument consisting in a fabric, wipe or sponge impregnated with a hygroscopic enzyme cleaning formulation containing one or more enzymes, one or more surfactants and an enzyme stabilising system.

31. A cleaning device according to claim 1 for use in cleaning an exterior surface of a tubular portion of an endoscope in need of said cleaning, said device including a pad having a groove extending from one end of the pad to an opposite end and adapted resiliently to engage the exterior surface of the tubular portion of the endoscope exterior surface, the pad being adapted alone or with a complementary pad to substantially encircle the exterior surface of the tubular portion and being resiliently deformable so as to engage the exterior surface of the encircled portion, whereby to uniformly wipe said exterior surface as the device is slid longitudinally along the endoscope tube.

32. A cleaning device according to claim 31 wherein the pad is formed of a needle felt and has two spaced apart parallel grooves each of arcuate cross-section which may be folded into alignment on opposite sides of a tubular axis to form a tubular tunnel resiliently engaging the exterior surface of a tubular portion of an endoscope about its circumference.

33. A cleaning device according to claim 32 which may be folded about a longitudinal fold seam.

34. A cleaning device according to claim 1 fabricated from a non-woven fabric and impregnated with one or more enzymes, one or more surfactants and at least one humectant.

35. A cleaning device according to claim 34 fabricated from a non-woven fabric and impregnated with a plurality of enzymes, a plurality of surfactants and at least one humectant.

36. A package containing a cleaning device for cleaning a surgical instrument, said cleaning device including at least one single use fabric, wipe or sponge impregnated with an enzyme, a surfactant, and a humectant.

37. A package according to claim 36 wherein the package is moisture permeable.

38. A method of cleaning the exterior surface of a surgical instrument in need thereof, said method including the steps of
  i) wiping the exterior surface, wherein a resilient pad or a wipe is pressed against an exterior surface of the surgical instrument and slid longitudinally to mechanically remove gross soiling and at the same time redistribute any residue remaining to a substantially uniform thickness, while at the same time
  ii) subjecting the surface to treatment with an enzyme and a surfactant, wherein the enzyme is present as a solution or a suspension in an amount of 5 to 25% w/w of the composition.

39. A method according to claim 38 wherein a resilient pad or wipe is held around a tubular portion of the surgical instrument in a manner which exerts a force acting radially towards an axis of the tubular portion of the surgical instrument.

40. A method according to claim 39 wherein the residue is redistributed to a more uniform thickness about a circumference and a length of the tubular portion of the surgical instrument.

* * * * *